United States Patent
Reimer

(10) Patent No.: US 11,364,120 B2
(45) Date of Patent: Jun. 21, 2022

(54) TRANSCATHETER MITRAL VALVE CHORDAE AUGMENTATION

(71) Applicant: St. Jude Medical, Cardiology Division, Inc., St. Paul, MN (US)

(72) Inventor: Jay Reimer, Saint Paul, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 167 days.

(21) Appl. No.: 16/405,227

(22) Filed: May 7, 2019

(65) Prior Publication Data

US 2019/0343632 A1    Nov. 14, 2019

Related U.S. Application Data

(60) Provisional application No. 62/668,430, filed on May 8, 2018.

(51) Int. Cl.
*A61F 2/24* (2006.01)
*A61B 17/04* (2006.01)

(52) U.S. Cl.
CPC .......... *A61F 2/2454* (2013.01); *A61F 2/2466* (2013.01); *A61B 17/0401* (2013.01); *A61F 2/2463* (2013.01)

(58) Field of Classification Search
CPC .... A61F 2/2454; A61F 2/2463; A61F 2/2457; A61F 2/2466; A61F 2/0811; A61F 2002/0864; A61B 17/0401; A61B 2017/00243
See application file for complete search history.

(56) References Cited

U.S. PATENT DOCUMENTS

| 8,303,622 | B2 | 11/2012 | Alkhatib | |
| 8,382,829 | B1* | 2/2013 | Call | A61F 2/2487 623/2.37 |
| 2003/0105519 | A1* | 6/2003 | Fasol | A61F 2/2457 623/2.1 |
| 2006/0095025 | A1* | 5/2006 | Levine | A61B 17/00234 606/17 |
| 2008/0228272 | A1 | 9/2008 | Moaddeb et al. | |
| 2010/0042147 | A1* | 2/2010 | Janovsky | A61B 17/0401 606/228 |
| 2010/0161042 | A1 | 6/2010 | Maisano et al. | |

(Continued)

OTHER PUBLICATIONS

International Search Report including the Written Opinion from Application No. PCT/US2019/031084 dated Aug. 1, 2019, pp. 1-12.

(Continued)

*Primary Examiner* — Katherine H Schwiker
*Assistant Examiner* — Raihan R Khandker
(74) *Attorney, Agent, or Firm* — Wei & Sleman LLP

(57) ABSTRACT

An apparatus for augmenting the length of native chordae tendineae to restore physiological leaflet coaptation. The apparatus includes a delivery device having a lumen therein which at least partially houses a prosthetic cord. The prosthetic cord has a first end with a first clasp configured to attach to a native chordae tendineae and a second end with a second clasp configured to attach to the native chordae tendineae. The native chordae tendineae is severed between the first clasp and the second clasp, and the length of the prosthetic cord between the first clasp and the second clasp is adjusted until physiological leaflet coaptation is restored.

8 Claims, 4 Drawing Sheets

(56) References Cited

U.S. PATENT DOCUMENTS

| | | |
|---|---|---|
| 2013/0190798 A1 | 7/2013 | Kapadia |
| 2016/0158008 A1* | 6/2016 | Miller .................. A61F 2/2427 623/2.11 |
| 2017/0290663 A1 | 10/2017 | Erickson et al. |
| 2019/0183648 A1* | 6/2019 | Trapp .................. A61F 2/2457 |

OTHER PUBLICATIONS

Trichon BH, et al, Relation of frequency and severity of mitral regurgitation to survival among patients with left ventricular systolic dysfunction and heart failure. The American journal of cardiology, Mar. 1, 2003, vol. 91(5): p. 538-543.

Mihos CG, Santana O. Mitral valve repair for ischemic mitral regurgitation: lessons from the Cardiothoracic Surgical Trials Network randomized study, Journal of thoracic disease. Jan. 27, 2016; vol. 8(1): pp. E94-E99.

Bursi F, et al, Heart failure and death after myocardial infarction in the community: the emerging role of mitral regurgitation. Circulation. Jan. 25, 2005, vol. 111(3): pp. 295-301.

Agricola E, et. al, Ischemic mitral regurgitation: mechanisms and echocardiographic classification. European journal of echocardiography: the journal of the Working Group on Echocardiography of the European Society of Cardiology, Jun. 30, 2007, vol. 9 (2), pp. 207-221.

* cited by examiner

TRANSCATHETER MITRAL VALVE CHORDAE AUGMENTATION

CROSS-REFERENCE TO RELATED APPLICATIONS

This application claims the benefit of the filing date of U.S. Provisional Patent Application No. 62/668,430 filed May 8, 2018, the disclosure of which is hereby incorporated herein by reference.

BACKGROUND OF THE INVENTION

The present invention generally relates to heart valve repair and, more particularly, to apparatus and methods for augmenting the chordae tendineae of heart valves.

Properly functioning heart valves can maintain unidirectional blood flow in the circulatory system by opening and closing, depending on the difference in the pressure on opposite sides of the valve. The two atrioventricular valves (mitral and tricuspid valves) are multicusped valves that prevent backflow from the ventricles into the atria during systole. They are anchored to the wall of the ventricle by chordae tendineae, which prevent the valve from inverting.

The mitral valve is located at the gate of the left ventricle and is made up of two leaflets and a diaphanous incomplete ring around the valve, known as the mitral valve annulus. When the valve opens, blood flows into the left ventricle. After the left ventricle fills with blood and contracts, the two leaflets of the mitral valve are pushed upwards and close, preventing blood from flowing back into the left atrium and the lungs.

Mitral valve tenting is a type of valve disease in which the mitral valve leaflets tent (i.e., a portion of the affected leaflet is bulged or raised), preventing the leaflets from properly coapting. Accordingly, as the ventricle contracts, blood is allowed to return to the left atrium and the lungs. This phenomenon is known as mitral regurgitation.

One cause of mitral valve tenting is shortened and/or inelastic chordae tendineae. For a variety of reasons, including trauma from cardiac infarction, chordae tendineae may shorten and/or lose flexibility. The shortened and/or inflexible chordae tendineae prevent the leaflets to which they are attached from properly coapting and result in ischemic mitral regurgitation. It has been discovered that as many as half of all myocardial infarction patients develop ischemic mitral regurgitation.

Untreated mitral regurgitation may lead to congestive heart failure and pulmonary hypertension. For this reason, mitral regurgitation is readily treated using annuloplasty rings, relocating papillary muscles, cutting chordae tendineae, or replacing the entire mitral valve.

Despite the various improvements that have been made to these devices and methods, various shortcomings remain. For example, these conventional methods typically require invasive open heart surgery, which often requires an extended recovery period.

There therefore is a need for improvements to the devices and methods for repairing tented mitral valve leaflets using minimally invasive techniques. Among other advantages, the present invention addresses these needs.

BRIEF SUMMARY OF THE INVENTION

In accordance with a first aspect of the present invention, a device for augmenting a shortened and/or inflexible native chordae tendineae is provided. The device advantageously allows the native chordae tendineae to be repaired using a minimally invasive technique that relieves mitral valve tenting and restores proper valve function.

One embodiment of the device includes a delivery device having a lumen, a cutting device at least partially disposed within the lumen for cutting a native chordae tendineae, and a prosthetic cord at least partially disposed within the lumen. The prosthetic cord has a first clasp provided at a proximal end of the prosthetic cord configured to attach to a first attachment site of the native chordae tendineae and a second clasp provided at a distal end of the prosthetic cord configured to attach to a second attachment site of the native chordae tendineae. A distance between the first attachment site and the second attachment site defines a native length and a distance along the prosthetic cord between the first clasp and the second clasp defines an augmented length. The augmented length is greater than the native length.

In a preferred embodiment, the prosthetic cord is elastic to mimic the natural properties of healthy chordae tendineae. Alternatively, the cord may be distensible or inelastic.

The delivery device may be a catheter. The cutting device may be a mechanical device such as a blade or scissors; or alternatively, may be a laser capable of severing the native chordae tendineae.

The first and second clasp may be mechanical clasps and/or formed of nitinol to grasp the first and second attachment sites of the native chordae tendineae. The first and second clasps may include a first and second indicator, respectively, such as a fluorescent band, for aiding a user in determining the augmented length.

Prior to attaching the first clasp to the first attachment site and the second clasp to the second attachment site, the prosthetic cord may be a single cord. Alternatively, prior to attaching the first clasp to the first attachment site and the second clasp to the second attachment site, the prosthetic cord may include a first prosthetic cord having an end attached to the first clasp and an unattached end and a second prosthetic cord having an end attached to the second clasp and an unattached end.

The device may further include a constraint ring for securing a first portion of the prosthetic cord to a second portion of the prosthetic cord. In another embodiment, the first portion of the prosthetic cord and the second portion of the prosthetic cord are configured to be tied or fused to one another.

A method of augmenting a native chordae tendineae is also provided. The method includes attaching a first clasp provided on a proximal end of a prosthetic cord to a first attachment site on the native chordae tendineae, attaching a second clasp provided on a distal end of the prosthetic cord to a second attachment site on the native chordae tendineae, and severing the native chordae tendineae at a location provided between the first attachment site and the second attachment site.

The method further includes determining an augmented length that restores physiological leaflet coaptation. The augmented length is defined by a distance along the prosthetic cord between the first clasp and the second clasp. The first and second clasp may include an indicator, which may be a fluorescent band, to aid the user in determining the augmented length.

A distance between the first attachment site and the second attachment site defines a native length. The augmented length is greater than the native length.

After the augmented length has been determined, a user may secure a first portion of the prosthetic cord to a second portion of the prosthetic cord to affix the prosthetic cord at the augmented length. The first portion of the prosthetic cord is secured to the second portion of the prosthetic cord via at least one of tying, fusing, and clamping.

BRIEF DESCRIPTION OF THE DRAWINGS

Various embodiments of the present disclosure are described herein with reference to the following drawings in which.

DETAILED DESCRIPTION

Figure 1:
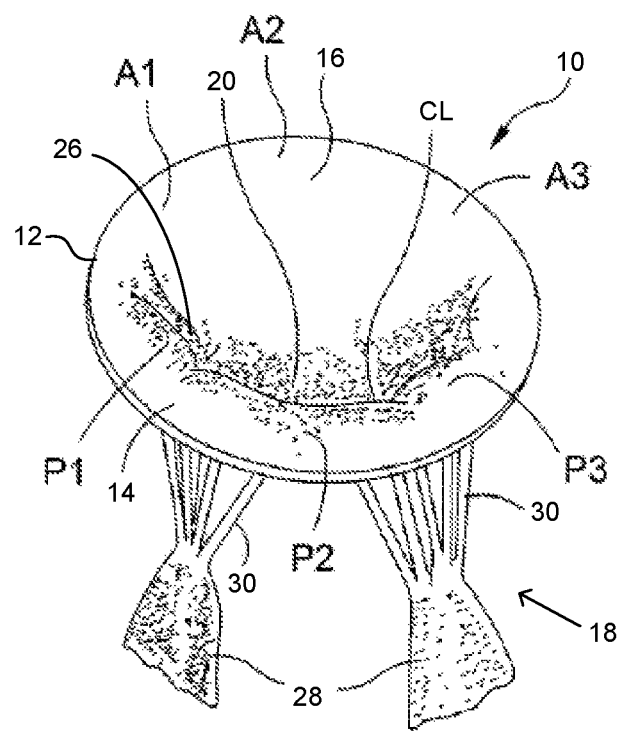
FIG. 1 is a diagrammatic perspective view of a mitral valve.

A typical mitral valve 10, an example of which is shown in FIG. 1, includes an annulus 12, a posterior leaflet 14, an anterior leaflet 16, and sub-valvular structure 18. Annulus 12 is a dense ring of fibrous tissue which lies at the juncture between the left atrium and the left ventricle. Posterior leaflet 14 and anterior leaflet 16 are attached to annulus 12 and extend toward the valve orifice. The portions of posterior and anterior leaflets 14, 16 that extend toward the valve orifice are known as free edges 20, 22. During systole, free edges 20, 22 meet at a coaptation line CL to close mitral valve 10.

Posterior and anterior leaflets 14, 16 each have an upper portion 24 that, when valve 10 is closed, extends from annulus 12 to coaptation line CL in a direction that is generally perpendicular to the direction of blood flow through the valve, and a lower portion 26 that, when the valve is closed, extends downward from the coaptation line to the free edge of the leaflet in a direction that is generally parallel to the direction of blood flow through the valve. Additionally, posterior leaflet 14 and anterior leaflet 16, respectively, have three scalloped portions P1, P2, P3 and A1, A2, A3, any of which may be tented.

Sub-valvular structure 18 includes two muscular projections that protrude from an inner wall of the left ventricle (not shown), known as papillary muscles 28, and numerous chordae tendineae 30, thin fibrous bundles that emanate from papillary muscles 28 and that are attached to an outflow surface of the valve leaflets near the free edges 20, 22 of scalloped portions P1, P2, P3, A1, A2, A3 or nearer the leaflet root. For a variety of reasons, ranging from natural causes to trauma from cardiac infarction, native chordae tendineae 30 may shorten and/or lose flexibility, or the ventricle may dilate, resulting in mitral valve tenting.

Figure 2:
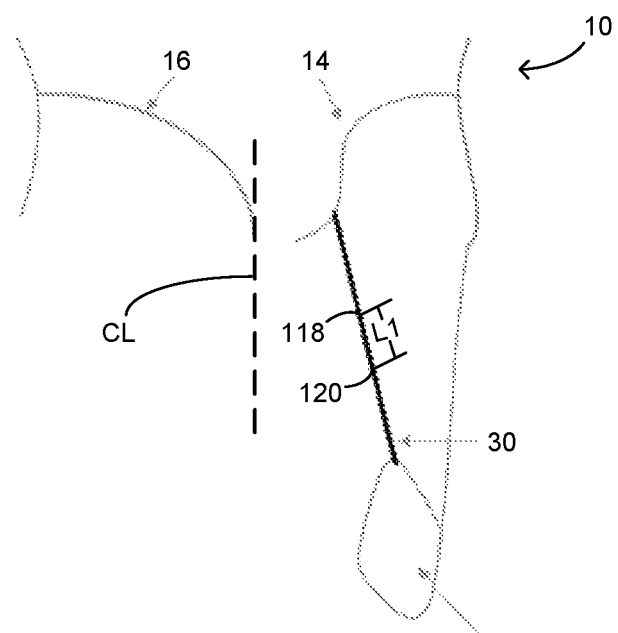
FIG. 2 is a schematic cutaway view of an exemplary tented mitral valve having a shortened native chordae tendineae.

FIG. 2 is a schematic representation of tented mitral valve 10 during systole (i.e., when a healthy mitral valve is closed). For clarity purposes, a single shortened or diseased chordae tendineae is depicted. Diseased chordae tendineae 30 is fully extended such that the free edge 20 of posterior leaflet 14 is prevented from extending to coaptation line CL and coapting with anterior leaflet 16. Furthermore, diseased chordae tendineae 30 causes posterior leaflet 14 to tent or bulge. For illustrative purposes, anterior leaflet 16 is depicted in a properly closed position (i.e., adjacent coaptation line CL), although it is understood that chordae tendineae attached to either or both posterior leaflet 14 and anterior leaflet 16 could be shortened. Additionally, as noted above, the tenting of posterior leaflet 14, or anterior leaflet 16, could result from dilation of the ventricle, in this case the left ventricle.

The devices and methods described herein are adapted to repair tented portions of posterior or anterior leaflets 14, 16. Instead of completely replacing the native valve, the devices augment damaged chordae tendineae and restore proper coaptation of the native heart valve leaflets. While the devices and methods are described in connection with the repair of the mitral valve, it will be appreciated that these concepts may be equally applicable in the repair of the tricuspid valve.

Figure 3:
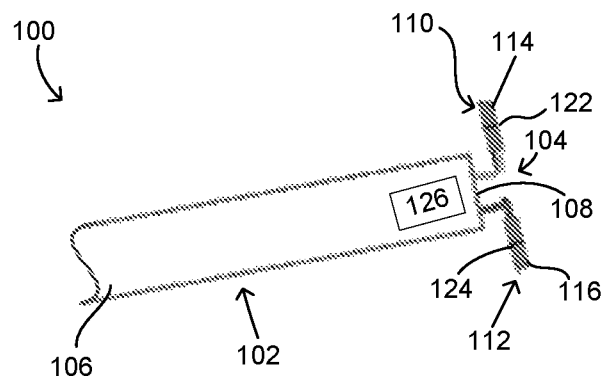
FIG. 3 is a schematic front view of an augmentation device according to an embodiment of the present disclosure.

Referring to FIG. 3, an exemplary device 100 for augmenting chordae tendineae includes an elongated catheter assembly 102 and a prosthetic cord 104. Catheter assembly 102 may be delivered to a site adjacent the patient's diseased chordae tendineae using a transfemoral, transapical, transseptal or other approach known in the art. Catheter assembly 102 includes a flexible elongated containment tube 106 that extends in a longitudinal direction and that has a lumen 108 for housing prosthetic cord 104.

Prosthetic cord 104 extends from a first or proximal end 110 to second or distal end 112. As shown in FIG. 3, an intermediate portion of prosthetic cord 104 between first end 110 and second end 112 is disposed within the lumen 108 of containment tube 106. Prosthetic cord 104 is adapted to augment or lengthen diseased chordae tendineae to relieve mitral valve tenting. Prosthetic cord 104 may be a single continuous cord or may be formed from two or more cords that are connected together prior to or during an augmentation procedure. In a preferred embodiment, prosthetic cord 104 is elastic to mimic the properties of natural, healthy chordae tendineae. In alternative arrangements, prosthetic cord 104 may be inelastic or may simply be stretchable.

A first clasp 114 is provided at the first end 110 of prosthetic cord 104 and a second clasp 116 is provided at the second end 112 of the prosthetic cord. The first clasp 114 is adapted to secure to a first attachment site 118 (shown in FIG. 2) of native chordae tendineae 30. Similarly, second clasp 116 is adapted to secure to a second attachment site 120 of native chordae tendineae 30. First and second attachment sites 118, 120 may be any two locations spaced apart from one another along the length of native chordae tendineae 30.

First and second clasps 114, 116 may, for example, be mechanically compressive clasps, for gripping the native chordae tendineae. In a first embodiment, clasps 114, 116 may include a pair of prongs formed from a plastically deformable material. When positioned around the native chordae tendineae 30, the prongs may be plastically deformed toward one another to secure clasps 114, 116 to the native chordae tendineae. In another embodiment, clasps 114, 116 may include a spring that biases the clasps to a closed configuration, much like a clothespin. To attach such clasps 114, 116 to the native chordae tendineae, the user may apply a force sufficient to overcome the biasing force, thereby transitioning the prongs of the clasps to an open configuration. Once properly positioned around native chordae tendineae 30, the force may be released to allow clasps 114, 116 to return to their closed configuration, thereby securing the clasps to the native chordae tendineae. In yet another embodiment, first and second clasps 114, 116 may be formed of nitinol or another shape-memory material adapted to change shape upon exiting lumen 108 to a configuration capable of grasping the natural chordae tendineae.

In any of the above described embodiments, clasps 114, 116 may also include barbs or have a roughened or sticky surface to improve the attachment forces between the clasps and native chordae tendineae 30. Clasps 114, 116 may additionally be semi-permeable and/or include bioactive molecules to promote tissue ingrowth of the native chord.

In a preferred embodiment, first clasp 114 includes a first indicator 122 and second clasp 116 includes a second indicator 124 for aiding a user in determining the relative locations of the first and second clasps 114, 116. First indicator 122 and second indicator 124 may be a fluorescent band. However, it is understood that first and second indicators 122, 124 may be any distinctive marking, for example, a radiopaque marking, detectable during an augmentation procedure that aids a user in determining the relative distance between first and second clasps 114, 116.

Augmentation device 100 may optionally include a cutting device 126 at least partially disposed within lumen 108 of containment tube 106 for severing the diseased chordae tendineae 30. Cutting device 126 may be a mechanical device, for example, a blade, a saw, or scissors. Cutting device 126 may alternatively be a laser or any other device capable of severing native chordae tendineae 30. In embodiments in which augmentation device 100 does not include a cutting device 126, the diseased chordae tendineae 30 may be severed using a separately introduced apparatus, including any of the devices just mentioned.

As is explained in more detail hereinafter, first attachment site 118 and second attachment site 120 are spaced a distance apart from one another. This distance is referred to herein as the native length L1.

Device 100 may be used to augment or lengthen diseased native chordae tendineae 30 to a length that relieves mitral valve tenting and restores proper valve function. This distance is referred to herein as the augmented length L2 (shown in FIG. 8) and is defined as the distance along prosthetic cord 104 between the first clasp 114 and the second clasp 116.

A clamp 128 (FIG. 7) may be applied to prosthetic cord 104 after prosthetic cord 104 has been adjusted to its proper augmented length L2. Clamp 128 constrains a first portion 130 of prosthetic cord 104 to a second portion 132 of the prosthetic cord so that the prosthetic cord is fixed at the proper augmented length L2. In one embodiment, clamp 128 is a constraining ring. It is also contemplated that first and second portions 130, 132 may alternatively be tied or fused together. In yet another embodiment, augmented length L2 may be preoperatively determined, thereby rendering the step of constraining first portion 130 to second portion 132 during the augmentation procedure unnecessary.

Figure 4:
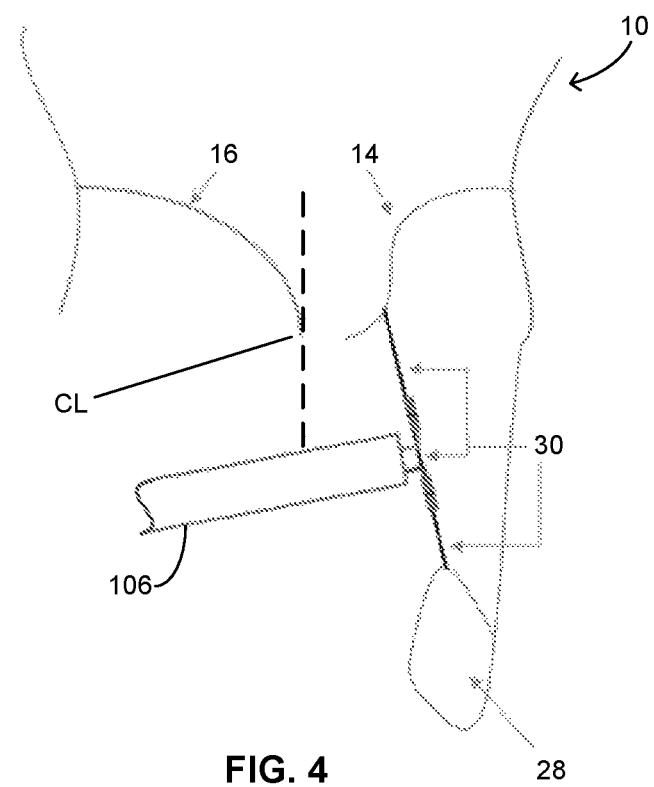
FIGS. 4-8 are schematic views showing the use of the augmentation device of FIG. 3 to apply clasps and a prosthetic cord to the native chordae tendineae to augment same.

The use of device 100 to augment diseased chordae tendineae will now be described with reference to FIGS. 4-8. Referring to FIG. 4, after catheter assembly 102 has been delivered to a surgical site adjacent diseased chordae tendineae 30, first and second clasps 114, 116 are deployed from lumen 108 of containment tube 106 and attached to first and second attachments sites 118, 120, respectively. First and second clasps 114, 116 may be individually deployed and attached to first and second attachment sites 118, 120, in either order, or deployed and attached simultaneously.

Figure 5:
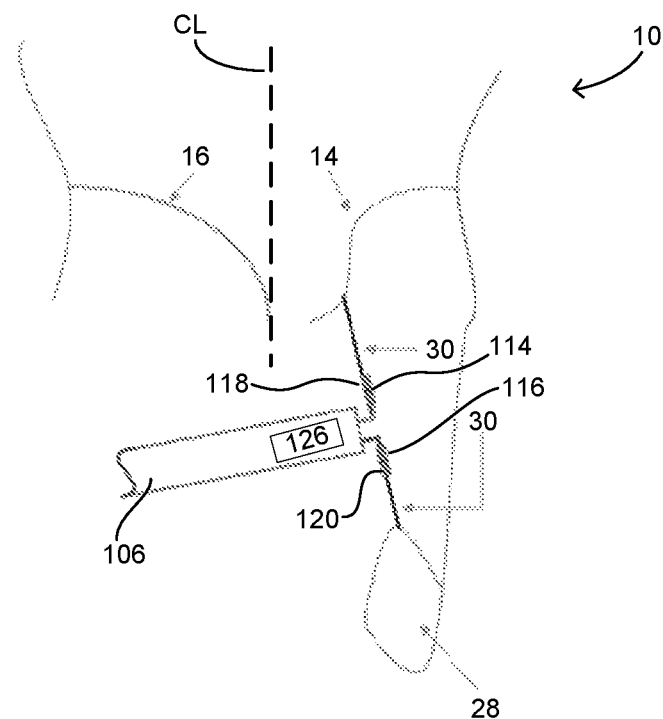
Figure 6:
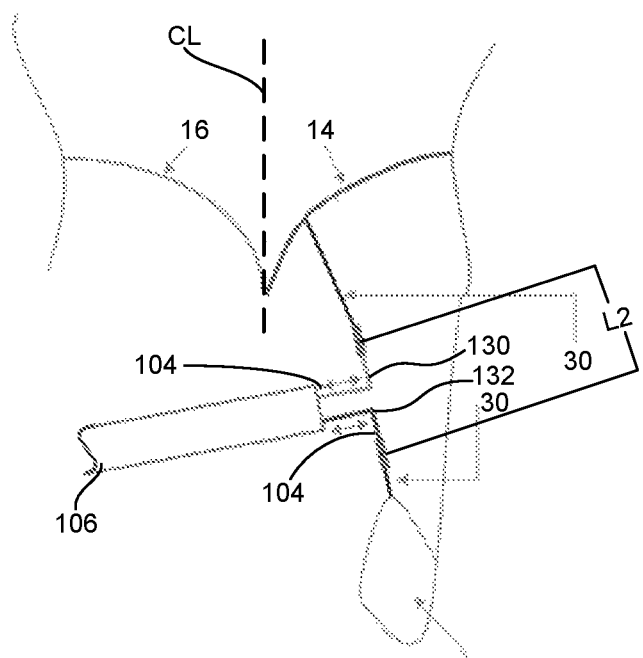

Referring to FIGS. 5 and 6, a surgeon, or other user performing the augmentation procedure, may then sever diseased chordae tendineae 30 using cutting device 126 or another device at a location between first and second clasps 114, 116. The surgeon may then manipulate the relative lengths of first portion 130 and second portion 132 of prosthetic cord 104 to modify the augmented length L2 until posterior leaflet 14 and anterior leaflet 16 properly coapt at coaptation line CL. More particularly, should it be desired to shorten the augmented length L2 of prosthetic cord 104, and hence the augmented length of chordae tendineae 30, the user may shorten one or both of first portion 130 and second portion 132 of the prosthetic cord by withdrawing a portion of the prosthetic cord, between the first and second portions into lumen 108 of containment tube 106. Alternatively, should it be desired to increase the augmented length L2 of prosthetic cord 104, and hence the augmented length of chordae tendineae 30, the user may feed an additional length of prosthetic cord 104 out from lumen 108 of containment tube 106 to lengthen one or both of first portion 130 and second portion 132. In either event, the user may cut excess portions of the native chordae tendineae using cutting device 126 or another device and withdraw the cut portions into lumen 108 of containment tube 106 for removal from the patient. Alternatively, the user may simply leave the excess portions of the native chordae tendineae in place where they will not interfere with the proper operation of mitral valve 10.

Figure 7:
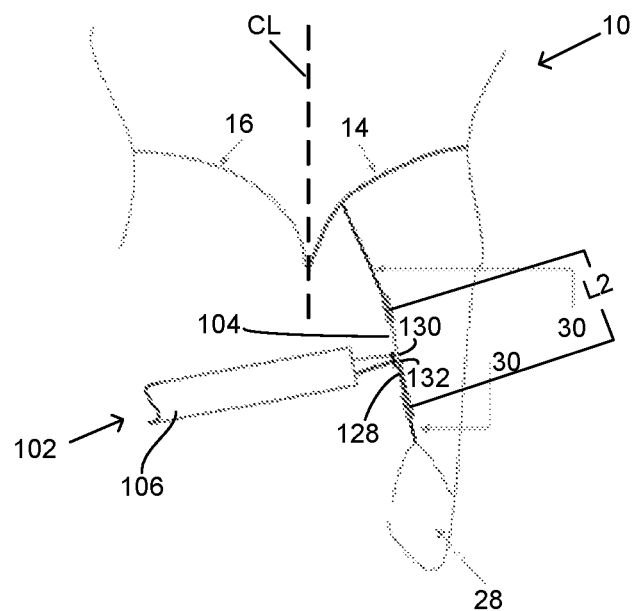

Referring to FIG. 7, when the proper augmented length L2 has been determined (i.e., an augmented length that allows posterior leaflet 14 and anterior leaflet 16 to properly coapt), clamp 128 may be slid over prosthetic cord 104 to clamp first portion 130 and second portion 132 of prosthetic cord 104 together, thereby fixing prosthetic cord 104 at the determined augmented length L2. One skilled in the art will appreciate that first and second indicators 122, 124 assist the surgeon in maintaining the appropriate augmented length L2 while clasp 128 is being applied.

It will be understood that if the proper augmented length L2 is preoperatively determined, and prosthetic cord 104 is manufactured or modified to be the proper augmented length L2 before being loaded into catheter assembly 102, the surgeon will not have to manipulate the first and second portions of prosthetic cord 104 relative to one another during the augmentation procedure or apply clamp 128. Instead, the augmentation procedure would end with the severing of diseased native chordae tendineae 30.

Figure 8:
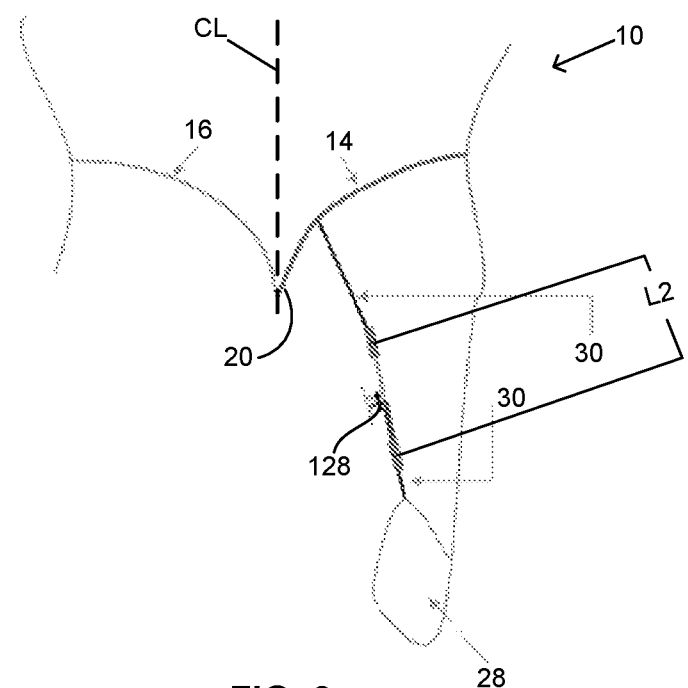

When the proper augmented length L2 has been determined during the augmentation procedure, excess prosthetic cord 104, located between first and second portions 130, 132, may optionally be removed by cutting with cutting device 126 or a separately introduced cutting device prior to withdrawing catheter assembly 102 from the patient. As is shown in FIG. 8, the augmented chordae tendineae 30 allows free edge 20 of posterior leaflet 14 to extend to coaptation line CL such that posterior leaflet 14 properly coapts with anterior leaflet 16. Tenting of posterior leaflet 14 is also obviated.

If the chordae tendineae augmentation does not completely alleviate valve tenting and restore proper coaptation, it will be understood that the same augmenting procedure may be repeated on another one or more chordae tendineae. Depending on the degree and location of the mitral valve tenting and the lack of coaptation, for example, it may be necessary to perform supplemental augmentations to the previously augmented chordae tendineae, to other chordae tendineae connected to the same scalloped portion, and/or to chordae tendineae connected to different scalloped portions or a different leaflet until mitral valve tenting is fully alleviated and physiological leaflet coaptation has been restored.

In a variant of augmentation device 100, rather than two clasps 114, 116, the device may initially include a single clasp having a weakened frangible area. In such variant, the single clasp is attached to both the first end 110 and the second end 112 of prosthetic cord 104 when the clasp is disposed within the lumen 108 of containment tube 106. After deployment, the single clasp may be loosely attached to chordae tendineae 30 and severed at the weakened frangible area, using cutting device 126 or another cutting device, to form two separate clasps. The surgeon may then slide one of the two clasps along chordae tendineae 30 to the first attachment site 118, where the clasp is then firmly secured, and the other of the two clasps to the second attachment site 120, where it is then firmly secured.

In another variant of augmentation device 100, rather than a single prosthetic cord 104, the device may initially include two separate and unconnected cords. In such variant, clasp 114 may be attached to one end of a first cord while the other end of the first cord is disposed within lumen 108 of containment tube 106. Clasp 116 may be attached to one end of a second cord while the other end of the second cord is disposed within lumen 108 of containment tube 106.

To perform a chordae tendineae augmentation using this variant, the surgeon may manipulate the lengths of a portion 130 of the first cord and a portion 132 of the second cord to modify the augmented length L2 until posterior leaflet 14 and anterior leaflet 16 properly coapt at coaptation line CL. More particularly, should it be desired to shorten the augmented length L2 of the prosthetic cord, and hence the augmented length of chordae tendineae 30, the user may withdraw one or both of the first and second cords into lumen 108 of containment tube 106. Alternatively, should it be desired to increase the augmented length L2 of the prosthetic cord, and hence the augmented length of chordae tendineae 30, the user may feed an additional length of one or both of the first and second cords out from lumen 108 of containment tube 106. After the two prosthetic cords have been adjusted to a proper augmented length L2, first portion 130 and second portion 132 may be clamped, tied, or fused to one another, as previously described, to form a single cord having the proper augmented length L2.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of augmenting the length of a native chordae tendineae, comprising:
   attaching a first end of a prosthetic cord to a first attachment site on the native chordae tendineae;
   attaching a second end of the prosthetic cord to a second attachment site on the native chordae tendineae;
   severing the native chordae tendineae at a location between the first attachment site and the second attachment site; and
   adjusting a length of the prosthetic cord in a linear direction between the first attachment site and the second attachment site to an adjusted length to restore physiological leaflet coaptation, wherein the prosthetic cord is partially colinear with the native chordae tendineae at the adjusted length.

2. The method of claim 1, wherein the attaching of the first end of the prosthetic cord to the first attachment site includes securing a first clasp on the first end of the prosthetic cord to the native chordae tendineae, and the attaching of the second end of the prosthetic cord to the second attachment site includes securing a second clasp on the second end of the prosthetic cord to the native chordae tendineae.

3. The method of claim 2, further comprising:
   adjusting the length of the prosthetic cord between the first clasp and the second clasp to the adjusted length.

4. The method of claim 3, wherein a distance between the first attachment site and the second attachment site prior to the severing of the native chordae tendineae defines a native chordae tendineae length, the adjusted length being greater than the native chordae tendineae length.

5. The method of claim 3, wherein the first clasp includes a first indicator and the second clasp includes a second indicator, the first indicator and the second indicator visually indicating the adjusted length.

6. The method of claim 5, wherein each of the first indicator and the second indicator includes a fluorescent band.

7. The method of claim 1, further comprising:
   securing a first portion of the prosthetic cord to a second portion of the prosthetic cord to fix the prosthetic cord at the adjusted length.

8. The method of claim 7, wherein the first portion of the prosthetic cord is secured to the second portion of the prosthetic cord via at least one of tying, fusing, or clamping.

* * * * *